United States Patent [19]

Eggler

[11] Patent Number: 5,665,749
[45] Date of Patent: Sep. 9, 1997

[54] BENZISOTHIAZOLES DERIVATIVES AS INHIBITORS OF 5-LIPOXYGENASE BIOSYNTHESIS

[75] Inventor: James Frederick Eggler, Stonington, Conn.

[73] Assignee: Pfizer Inc., New York, N.Y.

[21] Appl. No.: 716,341

[22] PCT Filed: Jan. 18, 1995

[86] PCT No.: PCT/IB95/00037

§ 371 Date: Sep. 30, 1996

§ 102(e) Date: Sep. 30, 1996

[87] PCT Pub. No.: WO95/26346

PCT Pub. Date: Oct. 5, 1995

Related U.S. Application Data

[63] Continuation of Ser. No. 218,788, Mar. 28, 1994, abandoned.

[51] Int. Cl.[6] .................. C07D 417/12; A01K 31/425
[52] U.S. Cl. ................................ 514/373; 548/210
[58] Field of Search .................... 548/210; 514/373

[56] References Cited

U.S. PATENT DOCUMENTS 5,134,148  7/1992  Crawley et al. ............... 514/312
5,196,419  3/1993  Crawley et al. ............... 514/241

FOREIGN PATENT DOCUMENTS 375404   6/1990   European Pat. Off. .
385662   9/1990   European Pat. Off. .
462813   12/1991  European Pat. Off. .
9205164  4/1992   WIPO .

OTHER PUBLICATIONS

H. Masamune and L.S. Melvin, Jr., Annual Reports in Medicinal Chemistry, 24, pp. 71–80 (Academic Press, 1989).

B. J. Fitzsimmons and J. Rokach, Leukotrienes and Lipoxygenases, pp. 427–502 (Elsevier, 1989).

*Primary Examiner*—Robert Gerstl
*Attorney, Agent, or Firm*—P. C. Richardson; Gregg C. Benson; John D. Conway

[57] ABSTRACT

This invention relates to new heterocyclic compounds which are selective inhibitors of 5-lipoxygenase (5-LO). The new heterocyclic compounds are useful in inhibiting 5-LO per se and in the treatment or alleviation of inflammatory disease or condition, allergy or cardiovascular diseases in mammals wherein the inflammatory disease or condition includes but is not limited to asthma, arthritis, bronchi chronic obstructive pulmonary disease, psoriasis, allergic rhinitis, dermatitis, shock, atopic dermatitis, rheumatoid arthritis or osteoa This invention also relates to pharmaceutical compositions useful therefor.

9 Claims, No Drawings

BENZISOTHIAZOLES DERIVATIVES AS INHIBITORS OF 5-LIPOXYGENASE BIOSYNTHESIS

This application a 371 of PCT/IB95/00037 filed Jan. 18, 1995 which is a continuation of 08/218788, filed Mar. 28, 1994 now abandoned.

BACKGROUND OF THE INVENTION

This invention relates to a series of substituted 1,1-dioxo [d]isothiazol-3-one compounds which are inhibitors of 5-lipoxygenase (5-LO) per se and as such are useful in the treatment or alleviation of inflammatory diseases or conditions, allergy and cardiovascular diseases in mammals wherein the inflammatory disease or condition includes but is not limited to asthma, arthritis, bronchitis, chronic obstructive pulmonary disease, psoriasis, allergic rhinitis, dermatitis, shock, atopic dermatitis, rheumatoid arthritis or osteoarthritis; and this invention also relates to pharmaceutical compositions useful therefor.

Arachidonic acid is known to be the biological precursor of several groups of endogenous metabolites, prostaglandins including prostacyclins, thromboxanes and leukotrienes. The first step of arachidonic acid metabolism is the release of esterified arachidonic acid and related unsaturated fatty acids from membrane phospholipids via the action of phospholipase. Free fatty acids are then metabolized either by cycloxygenase to produce the prostaglandins and thromboxanes or by lipoxygenase to generate hydroperoxy fatty acids which may be further converted to leukotrienes. Leukotrienes have been implicated in the pathophysiology of inflammatory diseases, including rheumatoid arthritis, gout, asthma, ischemia, reperfusion injury, psoriasis and inflammatory bowel disease. Any drug that inhibits lipoxygenase is expected to provide significant new therapy for both acute and chronic inflammatory conditions.

Recently, several review articles on lipoxygenase inhibitors have been reported. See, for example, H. Masamune and L. S. Melvin, Jr., in *Annual Reports in Medicinal Chemistry*, 24, 71–80 (Academic Press, 1989) and B. J. Fitzsimmons and J. Rokach in *Leukotrienes and Lipoxygenases*, 427–502 (Elsevier, 1989).

SUMMARY OF THE INVENTION

This invention is concerned with a series of substituted 1,1-dioxo[d]isothiazol-3-one compounds. These new compounds inhibit the production of 5-lipoxygenase (5-LO) in a mammal and as such are useful in the treatment or alleviation of inflammatory disease or condition, allergy and cardiovascular diseases in mammals wherein the inflammatory disease or condition includes but is not limited to asthma, arthritis, bronchitis, chronic obstructive pulmonary disease, psoriasis, allergic rhinitis, dermatitis, shock, atopic dermatitis, rheumatoid arthritis or osteoarthritis.

The compounds of the present invention are of the formula

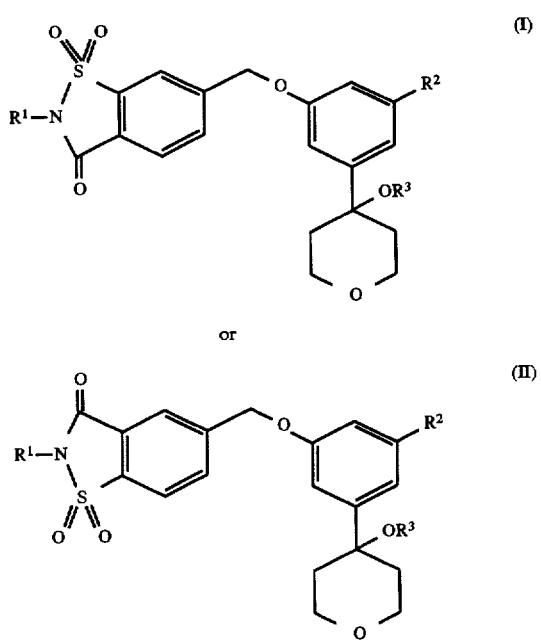

wherein $R^1$ is $(C_1-C_6)$alkyl, $(C_3-C_{10})$cycloalkyl, $(C_3-C_6)$alkenyl, $(C_3-C_6)$alkynyl or $(C_1-C_6)$alkyl-phenyl wherein the alkyl portion is optionally substituted by methyl or ethyl and the phenyl portion is optionally substituted by $(C_1-C_4)$alkoxy, $(C_1-C_4)$alkyl, F, Cl, Br or CF3;

$R^2$ is hydrogen or fluoro; and $R^3$ is hydrogen, methyl ethyl, propyl, isopropyl, $CF_2H$ or $CF_3$.

A preferred group of compounds are those compounds of the formula (I) or (II) wherein $R^1$ is $(C_1-C_6)$alkyl; $R^2$ is hydrogen or fluoro; and $R^3$ is hydrogen or methyl.

A particularly preferred group of compounds of the present invention are those compounds of formula (I) or (II) wherein $R^1$ is methyl or t-butyl; $R^2$ is fluoro; and $R^3$ is methyl.

A more particularly preferred group of compounds of the present invention are those compounds of formula (I) wherein $R^1$ is methyl or t-butyl; $R^2$ is fluoro; and $R^3$ is methyl.

Another more particularly preferred group of compounds of the present invention are those compounds of formula (II) wherein $R^1$ is methyl or t-butyl; $R^2$ is fluoro; and $R^3$ is methyl.

In a further aspect this invention provides pharmaceutical compositions comprising a compound of the formula (I) or (II) together with a pharmaceutically acceptable diluent or carrier which are useful in the inhibition of 5-LO per se and in the treatment or alleviation of inflammatory disease or condition, allergy or cardiovascular diseases in mammals wherein the inflammatory disease or condition include but are not limited to asthma, arthritis, bronchitis, chronic obstructive pulmonary disease, psoriasis, allergic rhinitis, dermatitis, shock, atopic dermatitis, rheumatoid arthritis or osteoarthritis in mammals, especially humans.

This invention also provides a method of inhibiting 5-LO in a mammal in need thereof which method comprises administering to said mammal a 5-LO inhibiting amount of a compound of the formula (I) or (II).

This invention further provides a method of treating or alleviating an inflammatory disease or condition, allergy or cardiovascular diseases in a mammal which comprises administering to said mammal an effective amount of a compound of the formula (I) or (II).

Further still, this invention provides a method of treating asthma, arthritis, bronchitis, chronic obstructive pulmonary disease, psoriasis, allergic rhinitis, dermatitis, shock, atopic dermatitis, rheumatoid arthritis or osteoarthritis in a mammal in need thereof which comprises administering to said mammal an effective amount of a compound of the formula (I) or (II).

As used herein and in the appendant claims the term alkyl encompasses both straight chain and branched alkyl groups, the term alkoxy encompasses both straight chain and branched groups and, the term cycloalkyl encompasses only monocycloalkyl groups.

DETAILED DESCRIPTION OF THE INVENTION

The compounds of the present invention having the formula (I) or (II) are readily and generally prepared by the following reaction processes.

A compound of the formula (III),

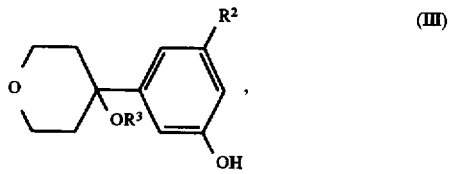

is reacted with a compound of the formula (IV),

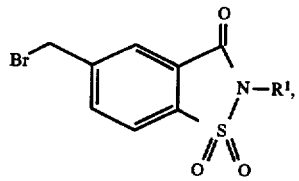

or formula (V),

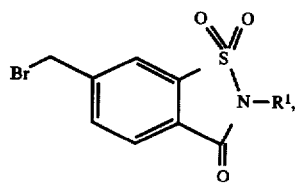

in the presence of a weak base, such as potassium carbonate, and in a reaction inert organic solvent, such as dimethylformamide. The reaction is stirred from 6 to 24 hours, preferably about 18 hours at room temperature, however, elevated temperatures may be employed. The mixture is worked-up according to standard procedures well known to those skilled in the art. The desired compound is isolated and purified by standard methods well known to those skilled in the art, such as column chromatography on silica gel or recrystallization using a solvent/non-solvent admixture system, such as methylene chloride/ether.

The preparation of the intermediate compounds are well known in the art and the preparation of certain intermediate compounds are described hereinbelow in Preparations.

The starting materials and reagents required for the synthesis of the compounds of the present invention are readily available either commercially, according to literature methods, or by methods exemplified in Preparations below.

The ability of the compounds of formula (I) or (II) to inhibit 5-LO and, consequently, demonstrate their effectiveness for treating or alleviating an inflammatory disease or condition, allergy or cardiovascular diseases in a mammal is shown by the following in vitro and in vivo assays.

Biological Assays

A23187-Induced Human Blood Leukotriene Release (5-LO)

Venous blood from healthy volunteers is collected in heparin (20 U/ml). Compounds are dissolved in DMSO. Each compound is tested at 4 concentrations. Zileuton (a 5-lipoxygenase inhibitor commercially available from Abbott Laboratories, batches of Zileuton can be synthesized in house according to synthetic procedures well-known in the art) and DMSO alone are used as positive and negative controls, respectively. 10 μl of compound or DMSO is added to glass borosilicate tubes (12×75 mm) and warmed to 37° C. One milliliter of whole blood is added to each tube. Following a 15 min. incubation period whole blood is stimulated with the calcium ionophore A23187 (commercially available from Sigma Chemical Co., St. Louis, Mo. 63178), at 50 μM for 1 hour. Tubes are immediately placed in a 4° C. centrifuge and spun at 1500× g to isolate plasma. A 50 μl volume of plasma is taken for measurement of leukotriene-B4 (LTB-4).

Samples are diluted 1:800 for assay by Leukotriene B4 Enzyme Immunoassay Kit (EIA) (Cayman Chemical Co., Ann Arbor, Minn.) using the manufacturer's instructions. A LTB-4 standard curve from 250 to 7.8 pg/ml is run with each plate. 50 μl of diluted sample is added per well 50 μl of LTB-4 acetylcholinesterase tracer followed by 50 μl of LTB-4 antiserum are then added. Plates are covered with plastic film and incubated for 18 hours at room temperature. Wells are emptied and rinsed 5 times with wash buffer prior to development with Ellman's Reagent (commercially available from Cayman Chemical, Ann Arbor, Minn.) in the dark for 1 hour at room temperature, or until the B0 (total absorbance) wells exhibit absorbance between 0.3 and 0.8 A.U. The plates are read at 405 nm using a THERMOmax microplate reader (Molecular Devices, Menlo Park, Calif.).

The LTB-4 standard curve is fitted to a semi-log equation. Absorbance values for experimental wells are averaged and the pg/ml LTB-4 concentration is determined by interpolating the average absorbance onto the standard curve. Percent inhibition is determined by the following equation: (-[(pg/ml) LTB-4 experimental/(pg/ml) LTB-4 DMSO control]-1) ×100. $IC_{50}$ is determined by linear regression of drug concentration plotted against inhibition and interpolation of the x value at y=50.

Aerosolized Antigen Induced Airway Obstruction

This assay tests the ability of a compound to block the airway obstruction resulting from an aerosolized antigen induced pulmonary anaphylaxis.

Male Hartley guinea pigs (300–350 g) are passively immunized by subcutaneous injection of 0.375 mg/kg of purified guinea pig anti-ovalbumin IgG1, 48–72 hours prior to antigen challenge. Pyrilamine (5 mg/kg) and propranolol (2 mg/kg) (both are commercially available from Sigma) are administered subcutaneously 30 minutes prior to challenge. Test compounds are administered into the stomach, either one or two hours prior to challenge, as a suspension in water and 2% Tween-80 (polyoxyethylene sorbitan monooleate, commercially available from Sigma, St. Louis, Mo.) using an Argyle feeding tube (commercially available from Sherwood Medical, St. Louis, Mo.).

Guinea pigs (5 test dose+5 controls) are then placed in a Tri-R Airborne infection apparatus (model A42, Rockwille Centre, N.Y. 11570). Ovalbumin (OA, 0.01–0.03%) is dissolved in 0.9% saline, placed in the glass nebulizer-venturi unit and aerosol generated for 5 minutes (main air flowmeter set at 10). This is followed by a 8 minute cloud decay (vacuum flow set at 7.0).

After removal, the animals are sacrificed by i.p. injection of about 2 ml Na-pentobarbital. The animals' pleural spaces are immediately opened by cutting into the xyphoid process allowing the lungs to collapse. Lungs are then removed, the heart cut away, and the trachea tied. The volume of trapped air in the lungs is determined by measuring the upward force exerted on a 20 g anchor, when the lungs and anchor are submerged in saline. The volume of trapped gas is normalized to the animals body weight and expressed as excised lung gas volume (ELGV) in ml/kg.

Interpretation:

A test compounds performance is judged by its ability to reduce the drug treated group mean ELGV below that of the control group mean ELGV. A loglinear regression ELGV=slope × log (dose)+ intercept is performed on the grouped mean data and an $ED_{50}$ is calculated as the dose necessary to produce a 50% reduction below the control group ELGV.

ELGV50% =((control ELGV−2)/2)+2).

Data are reported either as the $ED_{50}$ or as the % reduction in control ELGV.

% reduction=(control ELGV−test drug ELGV)/(control ELGV −2) at a given test drug dose.

For administration to humans to inhibit 5-LO and in the treatment of inflammatory diseases or conditions, allergy and cardiovascular diseases, oral dosages of the compounds of formula (I) or (II) are generally in the range of from 0.1–500 mg daily for an average adult patient (70 kg). Thus for a typical adult patient, individual tablets or capsules contain from 0.1 to 50 mg of active compound, in a suitable pharmaceutically acceptable vehicle or carrier. Multiple tablets or capsules may be required to meet the dosage requirements. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For human use, the compounds of the formula (I) or (II) can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules or ovales either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic. For topical administration, they are best used in the form of solutions, lotions, ointments, salves and the like.

The present invention is illustrated by the following examples, but it is not limited to the details thereof.

EXAMPLE 1

5-[3-Fluoro-5-(4-methoxy-tetrahydropyran-4-yl)-phenoxymethyl]-2-methyl-1,1-dioxo-benzo[d]isothiazole-3-one A mixture of 2-methyl-5-bromomethyl-1,1-dioxo-benzo[d]isothiazole-3-one (3.2 g), 4-(5-fluoro-3-hydroxyphenyl)-4-methoxytetrahydrofuran (2.4 g) and potassium carbonate (4.4 g) in 25 ml of dimethylformamide was stirred at room temperature for about 18 hours. The mixture was partitioned between ethyl acetate and water. The organic layer was separated, dried over sodium sulfate and evaporated. The residue was triturated with ether and filtered. The resulting solid was recrystallized from dichloromethane/ether to give 3 g of the title compound. m.p. 155°–156° C.

NMR (CDCl$_3$) δ: (1.95, m, 4H), (3.00, s, 3H), (3.33, s, 3H), 3.88, m, 4H), (5.25, s, 2H) (6.88–6.55, m, 3H), (7.40, m, 2H), (8.20, s, 1H).

EXAMPLE 2

5-[3-Fluoro-5-(4-methoxy-tetrahydropyran-4-yl)-phenoxymethyl]-2-t-butyl-1,1-dioxo-benzo[d]isothiazole-3-one Using a procedure analogous to that described in Example 1, from 768 mg (3.4 mmole) 4-(5-fluoro-3-hydroxyphenyl-4-methoxytetrahydrofuran, 970 mg (3.4 mmole) 2-t-butyl-5-bromomethyl-1,1-dioxobenzo[d]isothiazole-3-one and 1.4 g (10.2 mmole) K$_2$CO$_3$ there was obtained 783 mg of the title compound. m.p. : 123°–124° C.

NMR (CDCl$_3$) δ: (1.75, s, 9H), (2.00, m, 4H), (3.04, s, 3H), (3:84, m, 4H), (5.20, s, 2H) (6.60, d, 1H), (6.73, d, 1H), (6.83, s, 1H), (7.85, s, 2H), (8.08, s, 1H).

EXAMPLE 3

6-[3-Fluoro-5-(4-methoxy-tetrahydropyran-4-yl)-phenoxymethyl]-2-methyl-1, 1-dioxo-benzo[d]isothiazole-3-one Using a procedure analogous to that described in Example 1 from 2-methyl-6-bromomethyl-1,1-dioxobenzo[d]isothiazole-3-one (850 mg), 4-(5-fluoro-3-hydroxyphenyl)-4-methoxytetrahydrofuran (622 mg) and potassium carbonate (1.04 g) was obtained 231 mg of the title compound. m.p. 201°–202° C.

Mass Spectra: parent+18=454.

Preparation 1

3-Benzyloxy-1-bromo-5-fluorobenzene

Sodium hydride (60% w/w dispersion in mineral oil) 10.3 g was added portion-wise to a solution of benzyl alcohol (28.8 ml) in dimethylacetamide (400 ml) and the mixture stirred at room temperature for about 1 hour. 1-Bromo-3,5-difluorobenzene (50 g) was added dropwise. The mixture was stirred at room temperature for about 2 hours and the solvent was evaporated in vacuo. The residue was partitioned between methylene chloride and water and the organic phase was washed with water, dried over sodium sulfate and evaporated to give 90 g of crude product which was purified on silica gel eluting with methylene chloride/hexanes to give 47.7 g of the title compound as an oil.

NMR (CDCl$_3$) δ: (5.00, s, 2H), (6.62, dd, 1H), (6.85, dd, 1H), (6.93, s, 1H), (7.40, broad s, 5H).

Preparation 2

4-(3-Benzyloxy-5-fluorophenyl)-4-hydroxytetrahydropyran

A solution of 3-benzyloxy-1-bromo-5-fluorobenzene (29.1 g) in 250 ml of tetrahydrofuran was cooled to about −75° C. and n-butyl lithium (1.6M in hexane, 65 ml) was added dropwise.. The mixture was stirred at about −75° C. for about 1 hour and a solution of tetrahydropyran-4-one (10.4 g) was added dropwise. The mixture was stirred at about −75° C. for about 1 more hour then allowed to warm to about 0° C. A saturated aqueous solution of ammonium chloride was added and the tetrahydrofuran was evaporated in vacuo. The residue was partitioned between water and ethyl acetate. The organic phase was separated and dried over sodium sulfate. The residue was purified by column chromatography on silica gel eluting with methylene chloride/hexanes to give 9.2 g of the title compound as an oil.

NMR (CDCl$_3$) δ: (1.60, t, 2H), (2.15, m, 2H), (3.90, m, 4H), (5.05, s, 2H), (6.60, dd, 1H), (6.83, dd, 1H), (6.93, s, 1H), (7.40, broad s, 5H).

Mass Spectra: parent+1=302; base=285.

Preparation 3

4-(3-Benzyloxy-5-fluorophenyl)-4-methoxytetrahydrofuran

Sodium hydride (60% w/w dispersion in mineral oil, 1.3 g) was added to a solution of 4-(3-benzyloxy-5-fluorophenyl)-4-hydroxytetrahydrofuran (9.1 g) in tetrahydrofuran (30 ml). The mixture was stirred at room temperature for about 1 hour then cooled to about 0° C. with an ice-bath. Methyl iodide (4 ml) was added and the mixture stirred at room temperature for about 20 hours. The mixture was quenched with aqueous 10% hydrochloric acid (1 ml) and the tetrahydrofuran was evaporated in vacuo. The residue was partitioned between ethyl acetate and water. The organic phase was separated, dried over sodium sulfate and evaporated to give 5.9 g of the title compound as an oil.

NMR (CDCl$_3$) δ: (1.95, m, 4H), (2.98, s, 3H), (3.80, m, 4H), (5.05, s, 2H), (6.65, dd, 1H), (6.70, dd, 1H), (6.80, s, 1H), (7.40, m, 5H).

Preparation 4

4-(5-Fluoro-3-hydroxyphenyl)-4-methoxytetrahydrofuran

A solution of 4-(3-benzyloxy-5-fluorophenyl)-4-methoxytetrahydrofuran (1.1 g) in ethanol (20 ml) was hydrogenated in the presence of 10% palladium-on-charcoal catalyst (1 00 mg) for about 3 hours. The mixture was filtered and the filtrate was evaporated to give 840 mg of the title compound. m.p. 136°–137° C.

NMR (CDCl$_3$) δ: (1.95, m, 4H), (3.02, s, 3H), (3.85, m, 4H), (5.70, broad s, 1H), (6.50, d, 1H), (6.71, m, 2H).

Preparation 5

4-N-Dimethylbenzenesulfonamide

A solution of 4-methyl benzenesulfonyl chloride (15.2 g) in dichloromethane (300 ml) was cooled to about 0° C. in an ice-bath. Methylamine (40% solution in water, 18.6 g) was added dropwise. The mixture was stirred at room temperature. The organic layer was separated, dried over sodium sulfate and evaporated to give 14.5 g of the title compound. m.p. 82°–84° C.

Preparation 6

5-Methyl-2-methylsulfamoyl-benzoic acid

A solution of 4-N-dimethyl-benzenesulfonamide (14.5 g) in 300 ml of tetrahydrofuran was cooled to about 0° C. in an ice-bath. A solution of n-butyl lithium (1.6M in hexane, 98 ml) was added dropwise. The mixture was stirred and kept at room temperature for about 2 hours. Carbon dioxide gas was then bubbled into the yellow mixture over about 10 minutes. The mixture was partitioned between ethyl acetate and water. The aqueous layer was separated, acidified with concentrated hydrochloric acid and extracted with ethyl acetate. The organic extracts were dried over sodium sulfate and evaporated to a residue (14 g). The residue was triturated with dichloromethane and filtered to give 10 g of the title compound. m.p. 140°–141° C.

NMR (CDCl$_3$) δ: (2.48, s, 3H), (2.71, s, 3H), (5.81, broad s, 1H), (7.45, d, 1H), (7.76, s, 1H), (8.00, d, 1H), (8.30, broad s, 1H).

Mass Spectra: parent+18=247.

Preparation 7

2,5-Dimethyl-1,1-dioxo-benzo[d]isothiazole-3-one

Hydrogen chloride was bubbled into methanol (250 ml) over about 5 minutes. 5-Methyl-2-methylsulfamoyl-benzoic acid (10 g) was added in one portion. The mixture was heated on a steam bath for about 15 minutes then concentrated to a 50 ml volume. The mixture was cooled and filtered to give 6 g of the title compound. m.p. 131°–133° C.

NMR (CDCl$_3$) δ: (2.55, s, 3H), (3.26, s, 3H), (7.15, d, 1H), (7.73, m, 2H).

Preparation 8

2-Methyl-5-bromomethyl-1,1-dioxo-benzo[d]isothiazole-3-one

A solution of 2,5-dimethyl-1,1-dioxo-benzo[d]isothiazole-3-one (5.8 g) in carbon tetrachloride (100 ml) containing 2,2-azo-bis(2-methyl-propionitrile) (50 mg) and 4.8 g of N-bromosuccinimide was heated at reflux for about 2 hours.

The mixture was cooled to room temperature and filtered to remove succinimide. The filtrate was evaporated and the residue was triturated with methanol and filtered to give 2.5 g of the title compound. m.p. 110°–113° C.

NMR (CDCl$_3$) δ: (3.30, s, 3H), (4.55, s, 2H), (8.10–7.80, m, 3H).

Preparation 9

N-t-Butylbenzenesulfonamide

Using a procedure analogous to that described in Preparation 5, from 4-methylbenzenesulfonyl chloride (2.65 g) and t-butylamine (3.29 g) was obtained 3.0 g of the title compound: m.p. 77°–80° C.

Preparation 10

5-Methyl-2-(N-t-butylsulfamoyl)benzoic acid

Using a procedure analogous to that described in Preparation 6, from N-t-butylbenzenesulfonamide (13.6 g) and n-butyl lithium (1.6M in hexanes, 75 ml) was obtained 16 g of the title compound. m.p. 159°–162° C.

Preparation 11

5-Methyl-2-t-butyl-1,1dioxo-benzo[d]isothiazole-3-one

Using a procedure analogous to Preparation 7, from 5-methyl-2-(N-t-butylsulfamoyl)benzoic acid (16 g) was obtained 4 g of the title compound. m.p. 124°–125° C.

NMR (CDCl$_3$) δ: (1.80, s, 9H), (2.54, s, 3H), (7.60, d, 1H), (7.64, d, 1H), (7.8, s, 1H).

Preparation 12

2-t-Butyl-5-bromomethyl-1,1-dioxo-benzo [d] isothiazole-3-one

Using a procedure analogous to that described in Preparation 8, from 1.2 g of 2-t-butyl-5-methyl-1,1-dioxo-benzo [d]isothiazole-3-one was obtained 0.4 g of the title compound as an oil.

NMR (CDCl$_3$) δ: (1.75, s, 9H), (4.55, s, 2H), (7.60, d, 1H), (7.73, d, 1H), (7.80, s, 1H).

Preparation 13

3-N-Dimethylbenzenesulfonamide

Using a procedure analogous to that described in Preparation 5, from 3-methylbenzenesulfonyl chloride (15.2 g) and methylamine (40% solution in water, 18.6 g) there was obtained 13 g of the title compound.

NMR (CDCl$_3$) δ: (2.45, s, 3H), (2.65, d, 3H), (4.45, broad s, 1H), (7.40, m; 2H), (7.68, m, 2H).

Preparation 14

4-Methyl-2-methylsulfamoyl-benzoic acid

Using a procedure analogous to that described in Preparation 6, from 3-N-dimethyl benzenesulfonamide (10.2 g) and n-butyl lithium (1.6M in hexane, 69 ml) was obtained 5 g of the title compound.

NMR (CDCl$_3$) δ: (2.40, s, 3H), (2.50, d, 3H), (7.70–7.45, m, 3H), (13.50, broad s, 1H).

Mass Spectra: parent+18=247.

Preparation 15

2,6-Dimethyl-1,1-dioxo-benzo[d]isothiazole-3-one

Using a procedure analogous to that described in Preparation 7, from 4-methyl-2-methylsulfamoyl-benzoic acid (5 g) was obtained 2 g of the title compound.

NMR (CDCl$_3$) δ: (2.50, s, 3H), (3.15, s, 3H), (8.20–7.70, m, 3H).

Mass Spectra: parent+18=229.

Preparation 16

6-Bromomethyl-2-methyl-1,1-dioxo-benzo[d] isothiazole-3-one

Using a procedure analogous to that described in Preparation 8, from 2,6-dimethyl-1,1-dioxo-benzo[d]isothiazole-3-one (2 g), N-bromosuccinimide (1.7 g) and 2,2'-azo-bis (2-methyl-propionitrile) (10 mg) was obtained 650 mg of the title compound. m.p. 153°–154° C.

NMR (CDCl$_3$) δ: (3.30, s, 3H), (4.08, s, 2H), (8.10°–7.75, m, 3H).

Mass Spectra: parent+18=309.

What is claimed is:

1. A compound of the formula

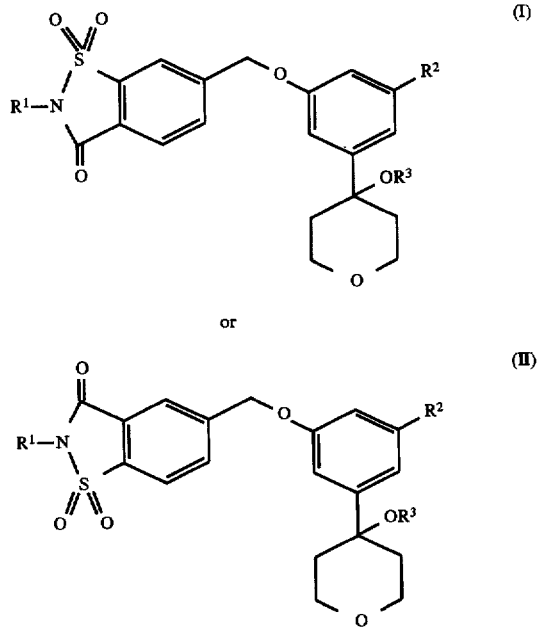

wherein

R$^1$ is (C$_1$–C$_6$)alkyl, (C$_3$–C$_{10}$)cycloalkyl, (C$_3$–C$_6$)alkenyl, (C$_3$–C$_6$)alkynyl or (C$_1$–C$_6$)alkyl-phenyl wherein the alkyl portion is optionally substituted by methyl or ethyl and the phenyl portion is optionally substituted by (C$_1$–C$_4$)alkoxy, (C$_1$–C$_4$)alkyl, F, Cl, Br or CF$_3$;

R$^2$ is hydrogen or fluoro; and

R$^3$ is hydrogen, methyl, ethyl, propyl, isopropyl, CF$_2$H or CF$_3$.

2. A compound according to claim 1 wherein R$^1$ is (C$_1$–C$_6$)alkyl.

3. A compound according to claim 2 wherein R$^1$ is methyl or t-butyl; R$^2$ is fluoro and R$^3$ is methyl.

4. A compound according to claim 3 of formula (I).

5. A compound according to claim 3 of formula (II).

6. A pharmaceutical composition comprising an amount of a compound according to claim 1 and a pharmaceutically acceptable diluent or carrier.

7. A method of inhibiting 5-lipoxygenase in a mammal in need thereof which comprises administering to said mammal a 5-lipoxygenase inhibiting amount of a compound according to claim 1.

8. A method of treating or alleviating an inflammatory disease or condition, allergy or cardiovascular disease in a mammal which comprises administering to said mammal an effective amount of a compound according to claim 1.

9. A method according to claim 8 wherein the inflammatory disease or condition is asthma, arthritis, bronchitis, chronic obstructive pulmonary disease, psoriasis, allergic rhinitis, dermatitis, shock, atopic dermatitis, rheumatoid arthritis or osteoarthritis.

* * * * *